US009868778B2

(12) United States Patent
Muraoka

(10) Patent No.: US 9,868,778 B2
(45) Date of Patent: Jan. 16, 2018

(54) ANTIBODY CAPABLE OF BINDING TO INFLUENZA VIRUS

(71) Applicant: Panasonic Intellectual Property Management Co., Ltd., Osaka (JP)

(72) Inventor: Jin Muraoka, Kyoto (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 127 days.

(21) Appl. No.: 14/995,902

(22) Filed: Jan. 14, 2016

(65) Prior Publication Data

US 2017/0037112 A1 Feb. 9, 2017

Related U.S. Application Data

(60) Provisional application No. 62/202,388, filed on Aug. 7, 2015.

(51) Int. Cl.
*C07K 16/10* (2006.01)
*C07K 19/00* (2006.01)

(52) U.S. Cl.
CPC ...... *C07K 16/1018* (2013.01); *C07K 2317/33* (2013.01); *C07K 2317/565* (2013.01); *C07K 2317/569* (2013.01); *C07K 2317/92* (2013.01)

(58) Field of Classification Search
CPC .......... C07K 2317/565; C07K 2317/56; C07K 2317/55; C07K 2317/51; C07K 2317/515
See application file for complete search history.

(56) References Cited

U.S. PATENT DOCUMENTS

2014/0302063 A1 10/2014 Hufton

FOREIGN PATENT DOCUMENTS

CN 103804493 5/2014

OTHER PUBLICATIONS

Hufton S. E. et al., "The Breadth of Cross Sub-Type Neutralisation Activity of a Single Domain Antibody to Influenza Hemagglutinin Can Be Increased by Antibody Valency", PLOS ONE [online], 2014, 9(8), e103294, pp. 1-19.

Jin Muraoka et al., "Development of Novel Biomaterial Capable of Recongizing Surface Protein of Influenza Virus" The Japan Society for Analytical Chemistry, Sep. 8, 2015.

*Primary Examiner* — Bao Li

(74) *Attorney, Agent, or Firm* — McDermott Will & Emery LLP

(57) ABSTRACT

The present invention provides a novel antibody capable of binding to an influenza virus. The antibody directed to the present invention consists of the amino acid sequence represented by SEQ ID NO: 15 or SEQ ID NO: 16.

2 Claims, 9 Drawing Sheets

FIG. 7

ANTIBODY CAPABLE OF BINDING TO INFLUENZA VIRUS

BACKGROUND

Incorporation by Reference—Sequence Listing

The material contained in the ASCII text file named "P681941_substitute_ST25.txt" created on Feb. 17, 2016 and having a file size of 19,218 bytes is incorporated by reference herein.

1. TECHNICAL FIELD

The present invention relates to an antibody capable of binding to an influenza virus.

2. DESCRIPTION OF THE RELATED ART

Patent Literature 1 discloses antibodies each capable of binding to an influenza virus. At least a part of the antibodies disclosed in Patent Literature 1 are derived from an alpaca. Patent Literature 1 is incorporated herein by reference.

CITATION LIST

Patent Literature

United States Patent Application Publication No. 2014/0302063

SUMMARY

An object of the present invention is to provide a novel antibody capable of binding to an influenza virus.

The present invention is an antibody that consists of an amino acid sequence, wherein said amino acid sequence consists of, in an N- to C-direction, the following structural domains:

N-FR1-CDR1-FR2-CDR2-FR3-CDR3-FR4-C
wherein
FR denotes a framework region amino acid sequence and CDR denotes a complementary determining region amino acid sequence;
the CDR1 consists of an amino acid sequence represented by GFTFERFDMG (SEQ ID NO: 1) or GRTFGAPYMA (SEQ ID NO: 2);
the CDR2 consists of an amino acid sequence represented by RFNSDDGRKSYADAVKG (SEQ ID NO: 3) or GDSTYYADSMKN (SEQ ID NO: 4);
the CDR3 consists of an amino acid sequence represented by SQAYTSSTDTSSTDAEDR (SEQ ID NO: 5) or DKWPFTGDVRSAGGYDY (SEQ ID NO: 6); and the antibody is capable of binding to an H1N1 influenza virus.

The present invention provides a novel antibody capable of binding to an influenza virus.

BRIEF DESCRIPTION OF THE DRAWINGS

FIG. 7 is a graph showing a SPR measurement result of an interaction between the VHH antibody consisting of the amino acid sequence represented by SEQ ID NO: 15 and a recombinant hemagglutinin protein.

DETAILED DESCRIPTION OF THE EMBODIMENT

Figure 1A:
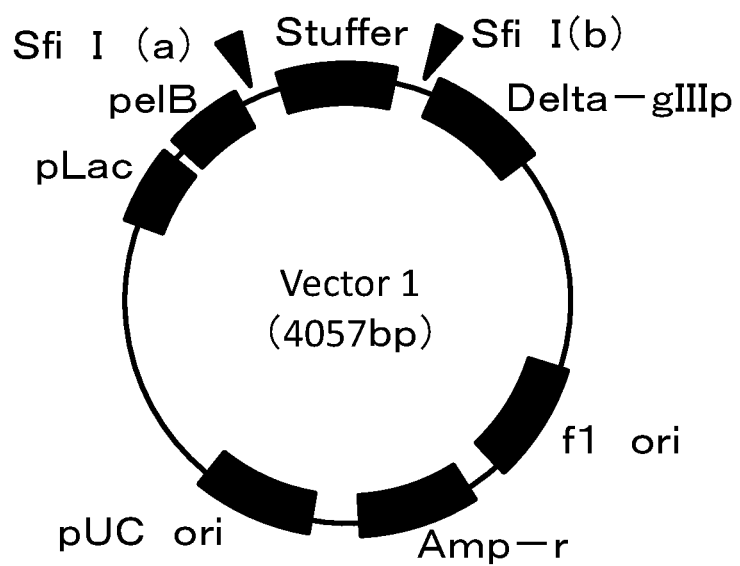
FIG. 1A is a map of a vector used to ligate various genes included in a gene library of a VHH antibody.

The antibody according to the present invention is capable of binding to an H1N1 influenza virus. As disclosed in Patent Literature 1, an antibody capable of binding to an H1N1 influenza virus consists of, in an N- to C-direction, an amino acid sequence consisting of the following structural domains.

N-FR1-CDR1-FR2-CDR2-FR3-CDR3-FR4-C
wherein
FR denotes a framework region amino acid sequence and CDR denotes a complementary determining region amino acid sequence.

In the present invention, the CDR1 consists of an amino acid sequence represented by GFTFERFDMG (SEQ ID NO: 1) or GRTFGAPYMA (SEQ ID NO: 2).

In the present invention, the CDR2 consists of an amino acid sequence represented by RFNSDDGRKSYADAVKG (SEQ ID NO: 3) or GDSTYYADSMKN (SEQ ID NO: 4).

In the present invention, the CDR3 consists of an amino acid sequence represented by SQAYTSSTDTSSTDAEDR (SEQ ID NO: 5) or DKWPFTGDVRSAGGYDY (SEQ ID NO: 6).

Desirably, the CDR1, the CDR2, and the CDR3 are represented by SEQ ID NO: 1, SEQ ID NO: 3 and SEQ ID NO: 5, respectively. In this case, more desirably, the FR1, the FR2, the FR3, and the FR4 consist of amino acid sequences represented by EVQLVESGGGFVQPGGSLRLSCVAS (SEQ ID NO: 7), WVRQAPGKSLEWVS (SEQ ID NO: 8), RFAISRDNAENTLYLQMNNLIPEDTATYYCVK (SEQ ID NO: 9), and GQGTQVTVSSEPKTPKPQSA (SEQ ID NO: 10), respectively. In other words, it is more desirable that the antibody according to the present invention consists of the following amino acid sequence.

(SEQ ID NO: 15)
EVQLVESGGGFVQPGGSLRLSCVASGFTFERFDMGWVRQAPGKSLEW

VSRFNSDDGRKSYADAVKGRFAISRDNAENTLYLQMNNLIPEDTATY

YCVKSQAYTSSTDTSSTDAEDRGQGTQVTVSSEPKTPKPQSA

The antibody consisting of the amino acid sequence represented by SEQ ID NO: 15 does not exhibit antibody cross reactivity with regard to an influenza virus other than an H1N1 influenza virus.

Alternatively, desirably, the CDR1, the CDR2, and the CDR3 are represented by SEQ ID NO: 2, SEQ ID NO: 4, and SEQ ID NO: 6, respectively. In this case, more desirably, the FR1, the FR2, the FR3, and the FR4 consist of the amino acid sequences represented by QVQLVESGGGLVQAGDSLRLSCAAA (SEQ ID NO: 11), WFRQAPGKEREFVAGISWS (SEQ ID NO: 12), RFTISRDNAKNTVYLQMNSLNPEDTAVYYCAA (SEQ ID NO: 13), and WGQGTQVTVSSEPKTPKPQSA (SEQ ID NO: 14), respectively. In other words, it is more desirable that the antibody according to the present invention consists of the following amino acid sequence.

```
                                      (SEQ ID NO: 16)
QVQLVESGGGLVQAGDSLRLSCAAAGRTFGAPYMAWFRQAPGKEREF

VAGISWSGDSTYYADSMKNRFTISRDNAKNTVYLQMNSLNPEDTAVY

YCAADKWPFTGDVRSAGGYDYWGQGTQVIVSSEPKTPKPQSA
```

Unlike the antibody consisting of the amino acid sequence represented by SEQ ID NO: 15, the antibody consisting of the amino acid sequence represented by SEQ ID NO: 16 exhibits antibody cross reactivity with regard to an influenza virus other than an H1N1 influenza virus.

EXAMPLES

Inventive Example 1

VHH antibodies capable of binding to hemagglutinin included in an influenza virus type A H1N1 were prepared in accordance with the following procedures. In the present specification, VHH (or VHH antibody) means a variable domain of a heavy chain of heavy chain antibody. HA means hemagglutinin.

(Immunization of Alpaca and Acquirement of Mononuclear Cell)

In order to form a VHH antibody gene library, an alpaca was immunized using a recombinant HA protein (available from Sino Biological, catalog number: 11055-V08H) derived from an Influenza virus type A H1N1 (A/California/04/2009) as an antigen.

Specifically, the recombinant HA protein having a concentration of 100 micrograms/milliliter was administered to the alpaca. After one week, the recombinant HA protein having the same concentration was administered to the alpaca, again. In this way, the alpaca was immunized with the recombinant HA protein five times for five weeks. After another week, blood of the alpaca was collected. Then, mononuclear cells were acquired from the blood as below.

A blood cell separation solution (available from COSMO BIO Co., Ltd., trade name: Lymphoprep) was added to a lymphocyte separation tube (available from Greiner Bio-One Co., Ltd., trade name: Leucosep). Then, the solution was subjected to centrifugation at 1,000×g at a temperature of 20 degrees Celsius for one minute.

The blood collected from the alpaca was treated with heparin. Then, an equivalent amount of phosphate buffered saline (hereinafter, referred to as "PBS") was added to the thus-treated blood to obtain a sample solution. Then, the sample solution was added to the lymphocyte separation tube containing the blood cell separation solution.

The lymphocyte separation tube was subjected to centrifugation at 800×g at a temperature of 20 degrees Celsius for thirty minutes.

The fraction containing the mononuclear cells was collected. PBS having three times volume was added. The fraction was subjected to centrifugation at 300×g at a temperature of 20 degrees Celsius for five minutes. The precipitate was suspended with PBS mildly. After the suspending, 10 microliters of the suspension was separated in order for the count of the number of cells. The remaining suspension was subjected to centrifugation at 300×g at a temperature of 20 degrees Celsius for five minutes.

An RNA storage solution (trade name: RNAlater) having a volume of 2 milliliters was added to the precipitate. Then, the solution was suspended mildly. The suspension was injected into two tubes each having a volume of 1.5 milliliters. Each tube included 1 milliliter of the suspension. The tube was stored at a temperature of −20 degrees Celsius. The suspension (5 microliters) separated for the count of the number of cells was mixed with a Türk's solution (15 microliters), and the number of the mononuclear cells was counted with a counting chamber.

(Formation of cDNA Gene Library of VHH Antibody)

Then, a total RNA was extracted from the mononuclear cells, and a cDNA gene library of VHH antibody was formed in accordance with the following procedure. In the following procedure, RNase-free-grade reagents and instruments were used.

A total RNA extraction reagent (trade name: TRIzol Regent, 1 milliliter) was added to the mononuclear cell fraction. The reagent was mixed mildly with the fraction, and left at rest at room temperature for five minutes. Chloroform (200 microliters) was added to the reagent, and the reagent was shaken strongly for fifteen seconds. The reagent was left at room temperature for two—three minutes. The reagent was subjected to centrifugation at 12,000×g at a temperature of 4 degrees Celsius for fifteen minutes or less.

The supernatant was moved to a new tube. RNase-free water and chloroform (200 microliters, each) were added to the tube. In addition, 500 milliliters of isopropanol was added to the tube. The liquid included in the tube was stirred using a vortex mixer. The liquid was left at rest at room temperature for ten minutes. Then, the liquid was subjected to centrifugation at 12,000×g or less at a temperature of 4 degrees Celsius for fifteen minutes. The supernatant was removed, and the precipitate was rinsed with 1 milliliter of 75% ethanol. This solution was subjected to centrifugation at 7,500×g or less at a temperature of four degrees Celsius for five minutes. The solution was dried to obtain total RNA. The obtained total RNA was dissolved in RNase-free water.

In order to obtain cDNA from the total RNA, a kit including a reverse transcriptase was employed. The kit was available from Takara Bio Inc., as a trade name of PrimeScript II 1st strand cDNA Synthesis Kit. The Random 6 mer and Oligo dT primer included in the kit were used as primers. The cDNA was obtained in accordance with the standard protocol attached to the kit.

The gene of the VHH antibody included in the alpaca was obtained from the cDNA by a PCR method. An enzyme for PCR was available from Takara Bio Inc., as a trade name of Ex-taq.

The following reagents were mixed to obtain a mixture solution.

| | |
|---|---|
| 10x buffer | 5 microliters |
| dNTPs | 4 microliters |
| Primer F | 2 microliters |
| Primer R | 2 microliters |
| cDNA template | 1 microliter |
| Ex-taq | 0.25 microliters |

The mixture solution was subjected to the following PCR method.

First, the mixture solution was heated at a temperature of 95 degrees Celsius for two minutes.

Then, the temperature of the mixture solution was varied in accordance with the following cycle.

Ninety six degrees Celsius for thirty seconds,
Fifty two degrees Celsius for thirty seconds, and
Sixty eight degrees Celsius for forty seconds
This cycle was repeated thirty times.

Finally, the mixture solution was heated at a temperature of sixty eight degrees Celsius for four minutes and stored at a temperature of four degrees Celsius.

The following primers were used in the present PCR method.

Primer 1:
(SEQ ID NO: 17)
5'-GGTGGTCCTGGCTGC-3'

Primer 2:
(SEQ ID NO: 18)
5'-ctgctcctcgcGGCCCAGCCGGCCatggcTSAGKTGCAGCTCGT
GGAGTC-3'

Primer 3:
(SEQ ID NO: 19)
5'-TGGGGTCTTCGCTGTGGTGCG-3'

Primer 4:
(SEQ ID NO: 20)
5'-TTGTGGTTTTGGTGTCTTGGG-3'

Primer 5:
(SEQ ID NO: 21)
5'-tttgCtctGCGGCCGCagaGGCCgTGGGGTCTTCGCTGTGGTGC
G-3'

Primer 6:
(SEQ ID NO: 22)
5'-tttgCtctGCGGCCGCagaGGCCgaTTGTGGTTTTGGTGTCTTG
GG-3'
(Reference literature: Biomed Environ Sci.,
2012; 27(2):118-121)

(Reference literature: Biomed Environ Sci., 2012; 27(2): 118-121)

Three PCR assays were conducted.

In the first PCR assay, a primer set A composed of the cDNA, Primer 1 and Primer 3 and a primer set B composed of the cDNA, Primer 1 and Primer 4 were used.

In the second PCR assay, a primer set C composed of the gene amplified with the primer set A, Primer 2, and Primer 3, and a primer set D composed of the gene amplified with the primer set B, Primer 2, and Primer 4 were used.

In the third PCR assay, a primer set E composed of the gene amplified with the primer set C, Primer 2, and Primer 5, and a primer set F composed of the gene amplified with the primer set D, Primer 2, and Primer 6 were used.

In this way, the gene library of the VHH antibody was formed. In other words, the gene library of the VHH antibody included the genes amplified with the primer sets E and F.

(Formation of Phage Library)

Next, a phage library was formed from the gene library of the VHH antibody in accordance of the following procedures.

Figure 1B:
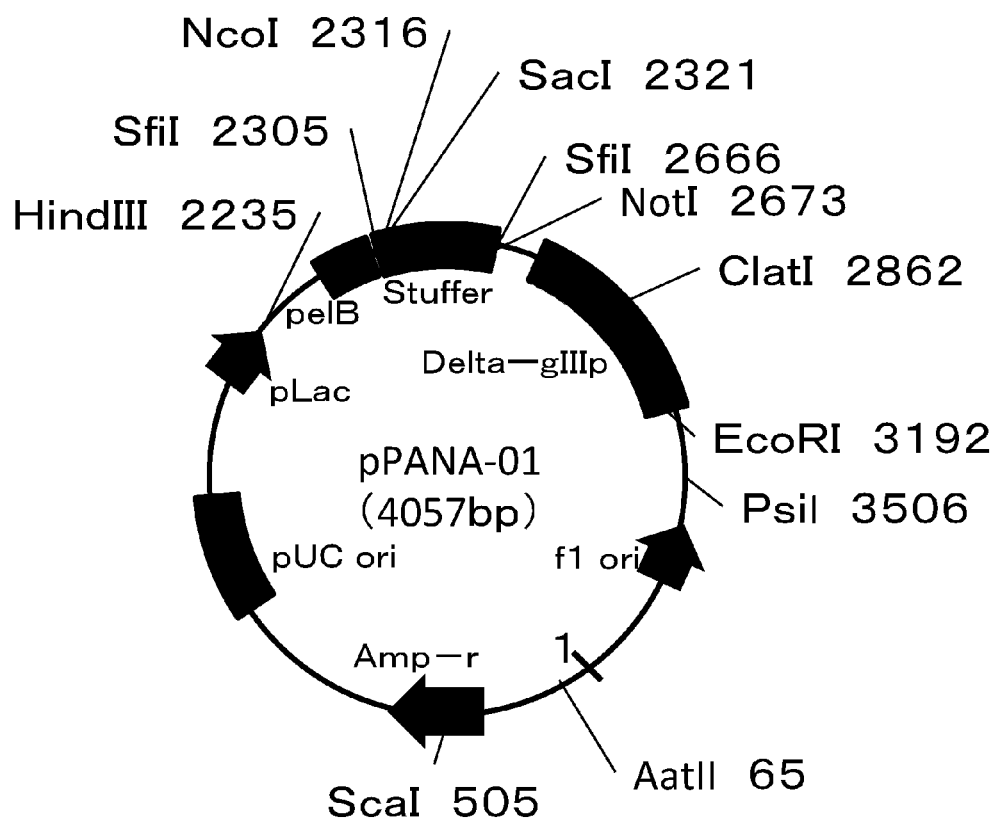
FIG. 1B shows the detail of the vector map shown in FIG. 1A.

A plasmid Vector 1 (4057 bp, see FIG. 1A) derived from a commercially available plasmid pUC119 (for example, available from TakaraBio Inc.,) was treated with a restriction enzyme SfiI. The restriction enzyme site SfiI(a) shown in FIG. 1 consists of the gene sequence represented by GGC-CCAGCCGGCC (SEQ ID NO: 23). The restriction enzyme site SfiI(b) consists of the gene sequence represented by GGCCTCTGCGGCC (SEQ ID NO: 24). FIG. 1B shows a detailed vector map of the plasmid Vector 1.

The plasmid Vector 1 consists of the following gene sequence.

(SEQ ID NO: 25)
gacgaaagggcctcgtgatacgcctattttataggttaatgtcatg ataataatggtttcttagacgtcaggtggcacttttcggggaaatgt gcgcggaacccctatttgtttattttctaaatacattcaaatatgt atccgctcatgagacaataaccctgataaatgcttcaataatattga aaaaggaagagtatgagtattcaacatttccgtgtcgcccttattcc cttttttgcggcattttgccttcctgttttttgctcacccagaaacgc tggtgaaagtaaaagatgctgaagatcagttgggtgcacgagtgggt tacatcgaactggatctcaacagcggtaagatccttgagagttttcg ccccgaagaacgttttccaatgatgagcacttttaaagttctgctat gtggcgcggtattatcccgtattgacgccgggcaagagcaactcggt cgccgcatacactattctcagaatgacttggttgagtactcaccagt cacagaaaagcatcttacggatggcatgacagtaagagaattatgca gtgctgccataaccatgagtgataacactgcggccaacttacttctg acaacgatcggaggaccgaaggagctaaccgcttttttgcacaacat gggggatcatgtaactcgccttgatcgttgggaaccggagctgaatg aagccataccaaacgacgagcgtgacaccacgatgcctgtagcaatg gcaacaacgttgcgcaaactattaactggcgaactacttactctagc ttcccggcaacaattaatagactggatggaggcggataaagttgcag gaccacttctgcgctcggcccttccggctggctggtttattgctgat aaatctggagccggtgagcgtgggtctcgcggtatcattgcagcact ggggccagatggtaagccctcccgtatcgtagttatctacacgacgg ggagtcaggcaactatggatgaacgaaatagacagatcgctgagata ggtgcctcactgattaagcattggtaactgtcagaccaagtttactc atatatactttagattgatttaaaacttcattttttaatttaaaagga tctaggtgaagatcctttttgataatctcatgaccaaaatcccttaa cgtgagttttcgttccactgagcgtcagacccgtagaaaagatcaa aggatcttcttgagatcctttttttctgcgcgtaatctgctgcttgc aaacaaaaaaaccaccgctaccagcggtggtttgtttgccggatcaa gagctaccaactctttttccgaaggtaactggcttcagcagagcgca gataccaaatactgtccttctagtgtagccgtagttaggccaccact -continued
tcaagaactctgtagcaccgcctacatacctcgctctgctaatcctg
ttaccagtggctgctgccagtggcgataagtcgtgtcttaccggtt
ggactcaagacgatagttaccggataaggcgcagcggtcgggctgaa
cgggggttcgtgcacacagcccagcttggagcgaacgacctacacc
gaactgagatacctacagcgtgagctatgagaaagcgccacgcttcc
cgaagggagaaaggcggacaggtatccggtaagcggcagggtcggaa
caggagagcgcacgagggagcttccaggggaaacgcctggtatctt
tatagtcctgtcgggtttcgccacctctgacttgagcgtcgattttt
gtgatgctcgtcaggggggcggagcctatggaaaaacgccagcaacg
cggccttttacggttcctggccttttgctggccttttgctcacatg
ttctttcctgcgttatccctgattctgtggataaccgtattaccgc
ctttgagtgagctgataccgctcgccgcagccgaacgaccgagcgca
gcgagtcagtgagcgaggaagcggaagagcgcccaatacgcaaaccg
cctctcccgcgcgttggccgattcattaatgcagctggcacgacag
gtttcccgactggaaagcgggcagtgagcgcaacgcaattaatgtga
gttagctcactcattaggcaccccaggctttacactttatgcttccg
gctcgtatgttgtgtggaattgtgagcggataacaatttcacacagg
aaacagctatgaccatgattacgccAAGCTTCGAAGGAGACAGTCAT
Aatgaaatacctgctgccgaccgctgctgctggtctgctgctcctcg
cGGCCCAGCCGGCCatggagcTCAAGATGACACAGACTACATCCTCC
CTGTCAGCCTCTCTGGGAGACAGAGTCACCATCAGTTGCAGGGCAAG
TCAGGACATTAGCGATTATTTAAACTGGTATCAGCAGAAACCAGATG
GAACTGTTAAACTCCTGATCTATTACACATCAAGTTTACACTCAGGA
GTCCCATCAAGGTTCAGTGGCGGTGGGTCTGGAACAGATTATTCTCT
CACCATTAGCAACCTGGAGCAAGAAGATATTGCCACTTACTTTTGCC
AACAGGGTAATACGCTTCCGTGGACGTTTGGTGGAGGCACCAAGCTG
GAAATCAAACGGGCTGATGCTGCACCAACTgtaGGCCtctGCGGCCG
CagaGcaaaaactcatctcagaagaggatctgaatggggccgcaTAG
ggttccggtgattttgattatgaaaagatggcaaacgctaataaggg
ggctatgaccgaaaatgccgatgaaaacgcgctacagtctgacgcta
aaggcaaacttgattctgtcgctactgattacggtgctgctatcgat
ggtttcattggtgacgtttccggccttgctaatggtaatggtgctac
tggtgattttgctggctctaattcccaaatggctcaagtcggtgacg
gtgataattcacctttaatgaataatttccgtcaatatttaccttcc
ctccctcaatcggttgaatgtcgcccttttgtctttagcgctggtaa
accatatgaattttctattgattgtgacaaaataaacttattccgtg
gtgtctttgcgtttcttttatatgttgccacctttatgtatgtattt
tctacgtttgctaacatactgcgtaataaggagtctTAATAAgaatt
cactggccgtcgttttacaacgtcgtgactgggaaaaccctggcgtt
acccaacttaatcgccttgcagcacatccccctttcgccagctggcg
taatagcgaagaggcccgcaccgatcgcccttcccaacagttgcgca -continued
gcctgaatggcgaatggcgcctgatgcggtattttctccttacgcat
ctgtgcggtatttcacaccgCATATGaAAATTGTAAgcgttaatatt
ttgttaaaattcgcgttaaattttttgttaaatcagctcatttttaa
ccaataggccgaaatcggcaaaatcccttataaatcaaaagaataga
ccgagatagggttgagtgttgttccagtttggaacaagagtccacta
ttaaagaacgtggactccaacgtcaaagggcgaaaaaccgtctatca
gggcgatggcccactacgtgaaccatcaccctaatcaagtttttttgg
ggtcgaggtgccgtaaagcactaaatcggaaccctaaagggagcccc
cgatttagagcttgacgggaaagccggcgaacgtggcgagaaagga
agggaagaaagcgaaaggagcgggcgctagggcgctggcaagtgtag
cggtcacgctgcgcgtaaccaccacaccgccgcgcttaatgcgccg
ctacaGGGCGCGTcccatATGgtgcactctcagtacaatctgctctg
atgccgcatagttaagccagccccgacaccgccaacacccgctgac
gcgccctgacgggcttgtctgctcccggcatccgcttacagacaagc
tgtgaccgtctccgggagctgcatgtgtcagaggttttcaccgtcat
caccgaaacgcgcga Similarly, the gene library of the VHH antibody was treated with the restriction enzyme SfiI. In this way, VHH antibody gene fragments were obtained.

The thus-treated plasmid Vector 1 was mixed with the VHH antibody gene fragments at a ratio of 1:2. An enzyme (available from Toyobo Co., Ltd., trade name: Ligation High ver. 2) was injected into the mixture solution. The mixture solution was left at rest at a temperature of 16 degrees Celsius for two hours. In this way, each of the VHH antibody gene fragments was ligated into the plasmid Vector 1.

*Coli* bacteria (available from Takara Bio Inc., trade name: HST02) were transfected using the thus-ligated plasmid Vector 1.

Then, the *coli* bacteria were incubated for fifteen hours on a 2YT plate culture medium containing ampicillin at a concentration of 100 micrograms/milliliter. In this way, obtained was a library of phages each of which displays a protein obtained from the gene fragment included in the gene library of the VHH antibody.

After the incubation, a concentration of the library was calculated by counting the number of single colonies formed on the 2YT plate culture medium. As a result, the library of the phages had a concentration of 2.6E+8/milliliter.

(Biopanning)

VHH antibodies capable of specifically binding to the HA protein were obtained from the phage library in accordance with the following procedures.

In order to extract the clones each capable of binding to the antigen from among the phages which expressed the VHH antibody, biopanning was conducted twice.

*Coli* bacteria (HST02) to which the VHH antibody gene fragment included in the gene library of the VHH antibody was introduced were incubated at a temperature of 30 degrees Celsius in the 2YT AG culture medium containing 100 micrograms/milliliter of ampicillin and 1% glucose in such a manner that a value $OD_{600}$ indicating absorbance reached 1.0. The 2YT AG culture medium has a volume of 100 milliliters. In this way, the *Coli* bacteria were proliferated.

Helper phages (available from Invitrogen company, trade name: M13K07) were added to the *coli* bacteria culture medium in such a manner that the multiplicity of infection (i.e., MOI) was approximately twenty.

Then, the culture medium was warmed for about thirty minutes at a temperature of 37 degrees Celsius. Then, the culture medium was subjected to centrifugation at a rotation speed of 4000 rpm for ten minutes to collect the *coli* bacteria. The *coli* bacteria were incubated overnight at a temperature of 30 degrees Celsius in 100 milliliters of a 2YTAK culture medium containing 100 micrograms/milliliter of ampicillin and 50 micrograms/milliliter of kanamycin, while subjected to centrifugation at 213 rpm.

The incubation liquid (100 milliliters) containing the thus-incubated *coli* bacteria were injected into two centrifugation tubes (volume: 50 milliliters, each). The two centrifugation tubes were subjected to centrifugation at a rotation speed of 4,000 rpm for ten minutes. Then, the supernatants (20 milliliters, each) were collected.

The supernatants (40 milliliters) were added to a 20% polyethylene glycol solution (10 milliliters) containing NaCl (2.5M). Then, the mixture solution was mixed upside down. Subsequently, the mixture solution was cooled on an ice for approximately one hour. The mixture solution was subjected to centrifugation at a rotation speed of 4,000 rpm for ten minutes. Then, the supernatant was removed. PBS containing 10% glycerol was injected toward the precipitate. Finally, the precipitate was loosened and dissolved. In this way, a library of phages each of which displays the VHH antibody was obtained.

(Screening of VHH Antibody Capable of Specifically Binding to HA)

(A) Immobilization of HA Antigen

HA was mixed with PBS to prepare an HA solution. The concentration of HA was 10 micrograms/milliliter. The HA solution (2 milliliters) was injected into an immunotube (available from NUNC Co. Ltd.). The HA solution was left at rest in the immunotube for one hour. In this way, HA was immobilized in the immunotube.

Then, the inside of the immunotube was washed three times with PBS.

The inside of the immunotube was filled with PBS which contained 3% skim milk (available from Wako Pure Chemical Industries, Ltd.). In this way, HA was blocked as an antigen in the immunotube.

The immunotube was left at rest at room temperature for one hour.

Subsequently, the inside of the immunotube was washed three times with PBS.

(B) Panning

The library of the phages each of which displays the VHH antibody (concentration: approximately 10E+11/milliliter) was mixed with 2 milliliters of PBS containing 3% skim milk to prepare a mixture solution. The mixture solution was injected into the immunotube in which the HA antigen was immobilized.

A lid formed of a parafilm was attached to the immunotube. Then, the immunotube was rotated upside down in a rotator for ten minutes.

The immunotube was left at rest at room temperature for one hour.

The inside of the immunotube was washed ten times with PBS containing 0.05% Tween 20. Hereinafter, such PBS is referred to as "PBST".

The inside of the immunotube was filled with PBST. Subsequently, the immunotube was left at rest for ten minutes. Then, the inside of the immunotube was washed ten times with PBST.

In order to extract phages each of which displays the VHH antibody bound to the HA antigen, a 100 mM trimethylamine solution (1 milliliter) was injected into the immunotube.

A lid formed of a parafilm was attached to the immunotube. Then, the immunotube was rotated upside down in a rotator for ten minutes.

In order to neutralize the solution, the solution was moved to a tube containing 1 mL of 0.5M Tris/HCl (pH: 6.8). Again, the extraction of the phage was repeated using a 100 mM trimethylamine solution (1 milliliter). In this way, 3 mL of the extraction liquid was obtained.

The extraction liquid (1 mL) was mixed with 9 mL of *coli* bacteria HST02. The mixture solution was left at rest for one hour at a temperature of 30 degrees Celsius.

In order to count the number of colonies, 10 microliters of the mixture solution containing the *coli* bacteria HST02 was distributed onto a small plate including a 2TYA culture medium (10 milliliters/plate).

The rest of the mixture solution was subjected to centrifugation. The supernatant was removed, and the precipitate was distributed onto a large plate including a 2TYA culture medium (40 milliliters/plate). These two plates were left at rest overnight at a temperature of 30 degrees Celsius. In this way, first panning was conducted.

Second panning was conducted identically to the procedure of the first panning. In other words, the panning was repeated. In this way, the monoclonal phages on which the VHH antibody was displayed were purified.

After the second panning, a colony of the *coli* bacteria was picked up with a toothpick. The picked-up one colony was put onto one well of a 96-flat-bottom plate. This was repeated. One well contained 200 microliters of a 2YTAG culture medium.

The solutions included in the wells were stirred at a rotation speed of 213 rpm at a temperature of 30 degrees Celsius.

The solution (50 microliters) containing grown *coli* bacteria was collected. The collected solution was mixed with 50 microliters of a 2YTA culture medium included in a plate. The 2YTA culture medium contained helper phages such that the MOI was set to be 20. The solution was left at rest at a temperature of 37 degrees Celsius for forty minutes.

The plate including the 2YTA culture medium was subjected to centrifugation at 1,800 rpm for twenty minutes. The supernatant was removed. The precipitate contained the *coli* bacteria. The precipitate was mixed with 200 microliters of a 2YTAK culture medium. The mixture solution was left at rest overnight at a temperature of 30 degrees Celsius.

The mixture solution was subjected to centrifugation at 1800 rpm for twenty minutes. The supernatant containing the *coli* bacteria was collected.

(C) Qualitative Evaluation of Phage-Displayed VHH Antibody and Antigen by ELISA

An HA protein solution having a concentration of 100 micrograms/milliliter was injected as an antigen into each of the wells of 96-well plate (available from Thermo Fischer Scientific, Inc., trade name: MaxiSorp). The volume of the HA protein solution in each well was 50 microliters. The 96-well plate was left at rest at room temperature for one hour. In this way, the HA antigen was immobilized in each well.

Each of the wells was washed three times with PBS. Then, PBS containing 3% skim milk (available from Wako Pure Chemical Industries, Ltd.) was injected into each well (200 microliters/well). The 96-well plate was left at rest at room temperature for one hour. In this way, the HA protein was blocked in each well. Subsequently, each well was washed three times with PBS.

The monoclonal phages each of which displays the VHH antibody were injected into each well (50 microliters/well). Then, the 96-well plate was left at rest for one hour. In this way, the phages reacted with the HA antigen.

Each well was washed three times with PBST. Then, an anti-M13 antibody (available from Abcam plc., trade name; ab50370, 10,000-fold dilution) was injected into each well (50 microliters/well). Then, each well was washed three times with PBST.

A color-producing agent (available from Thermo Fischer Scientific, Inc., trade name: 1-step ultra TMB-ELISA) was injected into each well (50 microliters/well). The 96-well plate was left at rest for two minutes to cause the color-producing agent to react with the antibody.

A sulfuric acid aqueous solution (normal, i.e., 1N) was injected into each well at a concentration of 50 microliters/well to cease the reaction.

The absorbance of the solution at a wavelength of 450 nanometers was measured.

Six wells each having a good absorbance measurement result were selected. The DNA sequences included in the phages contained in the selected six wells were analyzed by Greiner bio-one co., ltd. The analysis results of the DNA sequences will be described below. The following two DNA sequences were found.

(SEQ ID NO: 26)
GAGGTGCAGCTCGTGGAGTCTGGGGGAGGCTTTGTGCAGCCGGGGGG

GTCCCTGAGACTCTCCTGTGTAGCCTCTGGATTCACGTTCGAGCGTT

TTGACATGGGTTGGGTCCGCCAGGCTCCGGGAAAAAGCCTCGAGTGG

GTCTCGCGTTTTAATAGTGATGATGGTCGAAAAAGTTATGCGGACGC

CGTGAAGGGCCGATTCGCCATTTCCAGAGACAACGCCGAAAACACGC

TATATCTACAAATGAACAATCTGATACCTGAAGACACGGCCACTTAT

TATTGTGTGAAGTCTCAAGCTTACACATCTTCTACTGATACATCTTC

TACTGATGCCGAAGACAGGGGCCAGGGGACCCAGGTCACCGTCTCCT

CGGAACCCAAGACACCAAAACCACAATCGGCC (SEQ ID NO: 27)
CAGGTGCAGCTCGTGGAGTCTGGGGGAGGATTGGTGCAGGCTGGGGA

CTCTCTGAGACTCTCCTGTGCGGCCGCTGGACGCACCTTCGGTGCAC

CTTACATGGCCTGGTTCCGCCAGGCTCCAGGGAAGGAGCGTGAATTT

GTAGCAGGTATATCTTGGAGTGGTGATAGCACATACTATGCAGACTC

CATGAAGAACCGGTTCACCATCTCCAGAGACAACGCCAAGAACACGG

TGTATCTGCAAATGAACAGCCTAAACCCTGAGGACACGGCCGTTTAT

TACTGTGCAGCGGATAAGTGGCCCTTTACCGGTGATGTGCGGTCCGC

GGGGGGGTATGACTACTGGGGCCAGGGGACCCAGGTCACCGTCTCCT

CAGAACCCAAGACACCAAAACCACAATCGGCC

The protein synthesized from the DNA sequence represented by SEQ ID NO: 26 consists of the following amino acid sequence.

(SEQ ID NO: 15)
EVQLVESGGGFVQPGGSLRLSCVASGFTFERFDMGWVRQAPGKSLEW

VSRFNSDDGRKSYADAVKGRFAISRDNAENTLYLQMNNLIPEDTATY

YCVKSQAYTSSTDTSSTDAEDRGQGTQVTVSSEPKTPKPQSA

The protein synthesized from the DNA sequence represented by SEQ ID NO: 27 consists of the following amino acid sequence.

(SEQ ID NO: 16)
QVQLVESGGGLVQAGDSLRLSCAAAGRTFGAPYMAWFRQAPGKEREF

VAGISWSGDSTYYADSMKNRFTISRDNAKNTVYLQMNSLNPEDTAVY

YCAADKWPFTGDVRSAGGYDYWGQGTQVTVSSEPKTPKPQSA (Expression of Anti-H1N1 VHH Antibody)

Figure 2:
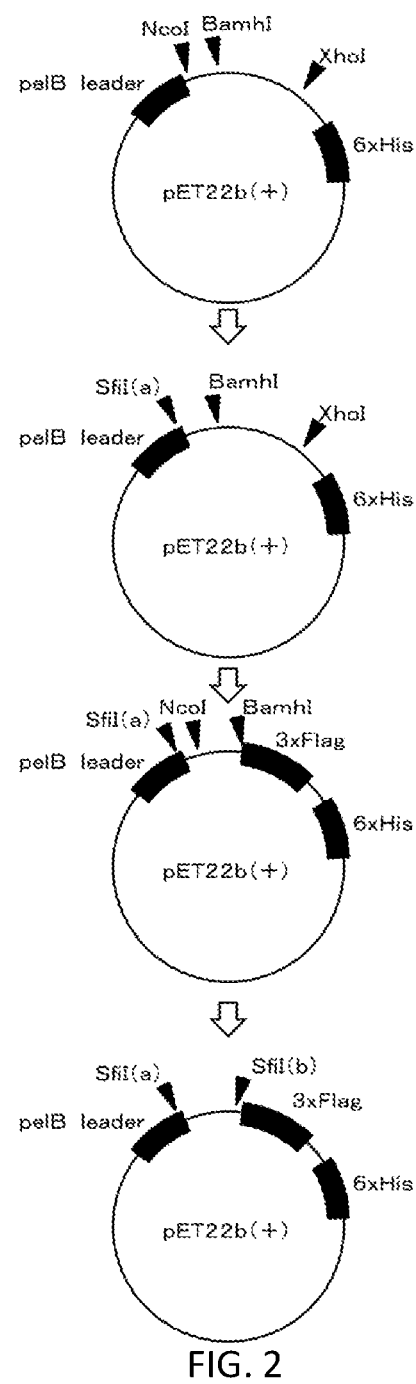
FIG. 2 shows a synthesis procedure of a vector used to express the VHH antibody.

A vector pET22b(+) was purchased from Merck Millipore Corporation. Using Prime Star Mutagenesis Basal Kit (available from Takara Bio Inc.), a 3× Flag tag and two restriction enzyme sites SfiI(a)(b) were added to the vector pET22b(+) by a PCR method. See FIG. 2. The procedure shown in FIG. 2 will be described below in more detail.

First, the restriction enzyme site SfiI(a) was add to the vector pET22b(+) by a PCR method using the following two primers and a restriction enzyme (available from Takara Bio Inc., trade name: Prime STAR MAX DNA polymerase).

Primer 1:
(SEQ ID NO: 28)
5'-GCCGGCTGGGCcGCGAGGAGCAGCAGACCA-3'

Primer 2:
(SEQ ID NO: 29)
5'-GCCCAGCCGGCcATGGCCATGGATATCGGA-3'

Then, a 3× Flag tag DNA fragment having restriction enzyme sites BamhI and XhoI at 5'-terminal end and 3'-terminal end respectively was formed by a PCR method using the following two primers and a restriction enzyme (available from Takara Bio Inc., trade name: Prime STAR MAX DNA polymerase).

Primer 1:
(SEQ ID NO: 30)
5'-CATGGATATCGGAATTAATTCggatccGACTACAAAGACCATGA

CGGTGATTATAAAGATCATGACATCctcgagCACCACCACCACCACC

ACTGA-3'

Primer 2:
(SEQ ID NO: 31)
5'-TCAGTGGTGGTGGTGGTGctcgagGATGTCATGATCTTTAT

AATCACCGTCATGGTTTTTGTAGTCggatccGAATTAATTCCGATAT

CCATG-3'

This 3× Flag tag DNA fragment and the vector pET22b(+) were treated with two restriction enzymes BamhI and XhoI (available from Takara Bio Inc.)

The 3× Flag tag DNA fragment was ligated into the vector pET22b(+) using Ligation Kit (available from Takara Bio Inc.). In this way, obtained was the vector pET22b(+) to which the 3× Flag tag and the restriction enzyme site SfiI (a) are added.

A DNA fragment having restriction enzyme sites NcoI and BamhI at 5'-terminal end and 3'-terminal end respectively was formed by a PCR method using the following two primers and a restriction enzyme (available from Takara Bio Inc., trade name: Prime STAR MAX DNA polymerase).

Primer 1:
(SEQ ID NO: 32)
5'-AAATACCTGCTGCCGccatggATATCGGAATTAATTCggcctct
gcggccGCAggatccGACTACAAAGACCAT-3'

Primer 2:
(SEQ ID NO: 33)
5'-ATGGTCTTTGTAGTCggatccTGCggccgcagaggccGAATTAA
TTCCGATATccatggCGGCAGCAGGTATTT-3'

Then, this DNA fragment and the vector pET22b(+) were treated with two restriction enzymes NcoI and BamhI (available from Takara Bio Inc.)

This DNA fragment was ligated into the vector pET22b(+) using Ligation Kit (available from Takara Bio Inc.). In this way, obtained was the vector pET22b(+) to which the 3× Flag tag and the restriction enzyme sites SfiI (a)(b) are added.

The sequence of the vector pET22b(+) was analyzed by Greiner bio-one co., td.

For the analysis of the sequence, a general T7 promoter primer set was used.

Selected were the vectors pET22b(+) which were confirmed through the analysis of the sequence to have been formed as planned.

Vectors pET22b(+) included in the liquid obtained by the PCR method were purified and collected into 50 microliters of diluted water using a DNA extraction kit (available from Promega KK). The thus-collected vectors pET22b(+) was treated with the SfiI restriction enzyme.

On the other hand, the plasmid Vector 1 into which the VHH antibody gene fragment included in the gene library of the VHH antibody was ligated was treated with the SfiI restriction enzyme. In this way, obtained were the following two DNAs (SEQ ID NO: 34 and SEQ ID NO: 35) including the gene sequence coding for the amino acid sequences represented by SEQ ID NO: 15 and SEQ ID NO: 16, respectively.

(SEQ ID NO: 34)
5'-GGCCCAGCCGGCCATGGCTGAGGTGCAGCTCGTGGAGTCTGGGG

GAGGCTTTGTGCAGCCGGGGGGTCCCTGAGACTCTCCTGTGTAGCC

TCTGGATTCACGTTCGAGCGTTTTGACATGGGTTGGGTCCGCCAGGC

TCCGGGAAAAAGCCTCGAGTGGGTCTCGCGTTTTAATAGTGATGATG

GTCGAAAAAGTTATGCGGACGCCGTGAAGGGCCGATTCGCCATTTCC

AGAGACAACGCCGAAAACACGCTATATCTACAAATGAACAATCTGAT

ACCTGAAGACACGGCCACTTATTATTGTGTGAAGTCTCAAGCTTACA

CATCTTCTACTGATACATCTTCTACTGATGCCGAAGACAGGGGCCAG

GGGACCCAGGTCACCGTCTCCTCGGAACCCAAGACACCAAAACCACA

ATCGGCCTCTGCGGCC-3'

(SEQ ID NO: 35)
5'-GGCCCAGCCGGCCATGGCTCAGGTGCAGCTCGTGGAGTCTGGGG

GAGGATTGGTGCAGGCTGGGGACTCTCTGAGACTCTCCTGTGCGGCC

GCTGGACGCACCTTCGGTGCACCTTACATGGCCTGGTTCCGCCAGGC

TCCAGGGAAGGAGCGTGAATTTGTAGCAGGTATATCTTGGAGTGGTG

ATAGCACATACTATGCAGACTCCATGAAGAACCGGTTCACCATCTCC

AGAGACAACGCCAAGAACACGGTGTATCTGCAAATGAACAGCCTAAA

CCCTGAGGACACGGCCGTTTATTACTGTGCAGCGGATAAGTGGCCCT

TTACCGGTGATGTGCGGTCCGCGGGGGGGTATGACTACTGGGGCCAG

GGGACCCAGGTCACCGTCTCCTCAGAACCCAAGACACCAAAACCACA

ATCGGCCTCTGCGGCC-3'

These two DNAs were treated with the SfiI restriction enzyme. Then, the thus-treated DNAs were collected by an electrophoresis method. Using a DNA ligation set (available from Takara Bio Inc.), the collected DNAs (SEQ ID NO: 36 and SEQ ID NO: 37) were ligated into the plasmid treated with the SfiI restriction enzyme.

(SEQ ID NO: 36)
5'-CGGCCATGGCTGAGGTGCAGCTCGTGGAGTCTGGGGGAGGCTTT

GTGCAGCCGGGGGGGTCCCTGAGACTCTCCTGTGTAGCCTCTGGATT

CACGTTCGAGCGTTTTGACATGGGTTGGGTCCGCCAGGCTCCGGGAA

AAAGCCTCGAGTGGGTCTCGCGTTTTAATAGTGATGATGGTCGAAAA

AGTTATGCGGACGCCGTGAAGGGCCGATTCGCCATTTCCAGAGACAA

CGCCGAAAACACGCTATATCTACAAATGAACAATCTGATACCTGAAG

ACACGGCCACTTATTATTGTGTGAAGTCTCAAGCTTACACATCTTCT

ACTGATACATCTTCTACTGATGCCGAAGACAGGGGCCAGGGGACCCA

GGTCACCGTCTCCTCGGAACCCAAGACACCAAAACCACAATCGGCCT

CTG-3'

(SEQ ID NO: 37)
5'-CGGCCATGGCTCAGGTGCAGCTCGTGGAGTCTGGGGGAGGATTG

GTGCAGGCTGGGGACTCTCTGAGACTCTCCTGTGCGGCCGCTGGACG

CACCTTCGGTGCACCTTACATGGCCTGGTTCCGCCAGGCTCCAGGGA

AGGAGCGTGAATTTGTAGCAGGTATATCTTGGAGTGGTGATAGCACA

TACTATGCAGACTCCATGAAGAACCGGTTCACCATCTCCAGAGACAA

CGCCAAGAACACGGTGTATCTGCAAATGAACAGCCTAAACCCTGAGG

ACACGGCCGTTTATTACTGTGCAGCGGATAAGTGGCCCTTTACCGGT

GATGTGCGGTCCGCGGGGGGTATGACTACTGGGGCCAGGGGACCCA

GGTCACCGTCTCCTCAGAACCCAAGACACCAAAACCACAATCGGCCT

CTG-3'

The ligation solution (2.5 microliters) and *coli* bacteria DH5α (available from Nippon Gene, 25 microliters) were mixed on an ice. The mixture solution was left at rest on the ice for six minutes. Then, the mixture solution was heated at a temperature of 42 degrees Celsius for forty five seconds. Finally, the mixture solution was left at rest on the ice for one minute. This procedure is known as a general heat shock method.

The total amount of the mixture solution was distributed onto a LBA culture medium containing ampicillin at a concentration of 100 micrograms/milliliter. The LBA culture medium was left at rest overnight at a temperature of 37 degrees Celsius.

Three colonies were selected from among the colonies formed on the LBA culture medium. The selected three colonies were incubated overnight in the LBA culture medium (3 milliliters).

The plasmids contained in the incubated *coli* bacteria were extracted from the LBA culture medium using a plasmid extraction kit (available from QIAGEN, trade name: QIAprepspin miniprep kit). In order to confirm that the gene of the targeted VHH antibody was inserted in the plasmid, the sequence of the plasmid was analyzed by Greiner bio-one co., ltd. For the analysis of the sequence, a general T7 promoter primer set was used.

Selected were plasmids which were confirmed through the analysis of the sequence to be formed as planned.

*Coli* bacteria (Competent Cell BL21 (DE3) pLysS, available from Life Technologies Corporation) were transfected using the selected plasmids.

An SOC culture medium (50 microliters) was injected into the solution containing the transfected *coli* bacteria. Then, the *coli* bacteria were rescued at a temperature of 37 degrees Celsius for one hour, while shaken at 213 rpm.

Then, the *coli* bacteria solution was collected. The collected *coli* bacteria solution (5 milliliters) was distributed onto a LBA culture medium. The LBA culture medium was left at rest overnight at a temperature of 37 degrees Celsius.

One colony was selected from among the colonies formed in the LBA culture medium. The selected colony was picked up with a toothpick. The picked-up colony was incubated in a LBA culture medium (3 milliliters) at a temperature of 37 degrees Celsius, while shaken at 213 rpm. In this way, a culture liquid was obtained.

In addition, the culture liquid (25 milliliters) was mixed with a LBA culture medium (500 milliliters). Until the absorbance of the mixture solution at a wavelength of 600 nanometers was 0.5, the mixture solution was shaken at 160 rpm at a temperature of 37 degrees Celsius.

After the absorbance was 0.5, an isopropylthiogalactoside solution (hereinafter, referred to as "IPTG solution") was added to the mixture solution. The final concentration of the IPTG solution was 1 mM. The *coli* bacteria contained in the mixture solution were incubated at a temperature of 37 degrees Celsius for six hours. In order to collect the thus-incubated *coli* bacteria, the mixture solution was subjected to centrifugation at 6,000 rpm for ten minutes at a temperature of 4 degrees Celsius.

The collected *coli* bacteria were mixed with PBS having ten times volume. The mixture solution was stirred using a vortex mixer. In this way, the *coli* bacteria were washed. Then, the mixture solution was subjected to centrifugation at 6,000 rpm for ten minutes at a temperature of 4 degrees Celsius to collect *coli* bacteria. The collected *coli* bacteria were mixed again with PBS having ten times volume. The *coli* bacteria contained in the mixture solution were disintegrated using an ultrasonic wave.

The disintegration liquid containing *coli* bacteria was subjected to centrifugation at 10,000 rpm for fifteen minutes at a temperature of 4 degrees Celsius. The supernatant was collected. The collected supernatant was filtered through a 0.45-micrometer filter.

The filtrate was purified using His-trap (available from GE healthcare) in accordance with a recommended protocol. In the purification, an elution buffer having a total amount of 3 microliters was used for 1 milliliter of the filtrate. The buffer solution contained in the filtrate was substituted with PBS, using PD-10 (available from GE healthcare). In the substitution, PBS having a total amount of 2.5 microliters was used for 1 milliliter of the filtrate. In this way, a solution containing the anti-H1N1 antibody was obtained.

The anti-H1N1 antibody contained in the thus-obtained solution was quantified using an absorption spectrometer (available from Scrum Inc., trade name: nanodrop) on the basis of the absorption measurement value at a wavelength of 280 nanometers. As a result, the concentration of the anti-H1N1 antibody was 4 milligrams/milliliter.

(D-1) Surface Plasmon Resonance Evaluation of Anti-H1N1 Antibody Using Recombinant HA The anti-H1N1 antibody was evaluated as below using a recombinant HA and a surface plasmon resonance evaluation device. The details of the surface plasmon resonance (hereinafter, referred to as "SPR") will be described below.

SPR evaluation device: T200 (available from GE Healthcare) Immobilization buffer: HBS-EP (available from GE Healthcare) Running buffer: HBS-EP+ (available from GE Healthcare) Sensor chip: CM5 (available from GE Healthcare) Immobilization reagents: N-Hydroxysuccinimide (NHS) and N-[3-(Dimethylamino)propyl]-N'-ethylcarbodiimide (EDC)

HA: recombinant hemagglutinin (HA) protein derived from influenza virus subtype H1N1 (available from Sino Biological Inc., trade name: 11055-V08H)

HA was immobilized in accordance with the wizard included in the control software of the SPR evaluation device T200. For the immobilization of HA, an acetic acid solution having a pH of 5.0 was used. The acetic acid solution had a concentration of 1 microgram/mil iliter. The immobilization amount was set to be 250 RU.

Figure 3:
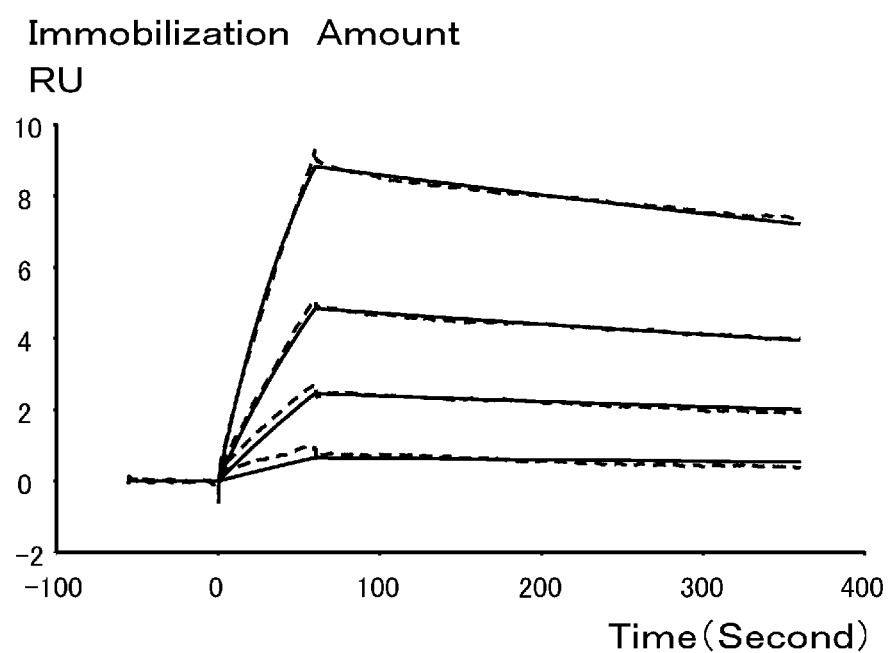
FIG. 3 is a graph showing a SPR evaluation result in a case of using the VHH antibody consisting of the amino acid sequence represented by SEQ ID NO: 15.

The anti-H1N1 antibody consisting of the amino acid sequence represented by SEQ ID NO: 15 was used as an analyte. In the first to fourth analyses, the concentrations of the anti-H1N1 antibody contained in the running buffer were adjusted to 100 nM, 50 nM, 25 nM, and 12.5 nM, respectively. FIG. 3 is a graph showing the evaluation result obtained from the SPR evaluation device T200. The dissociation constant Kd was calculated using the evaluation software (available from GE Healthcare). As a result, the dissociation constant Kd was 4.95 nM.

Figure 4:
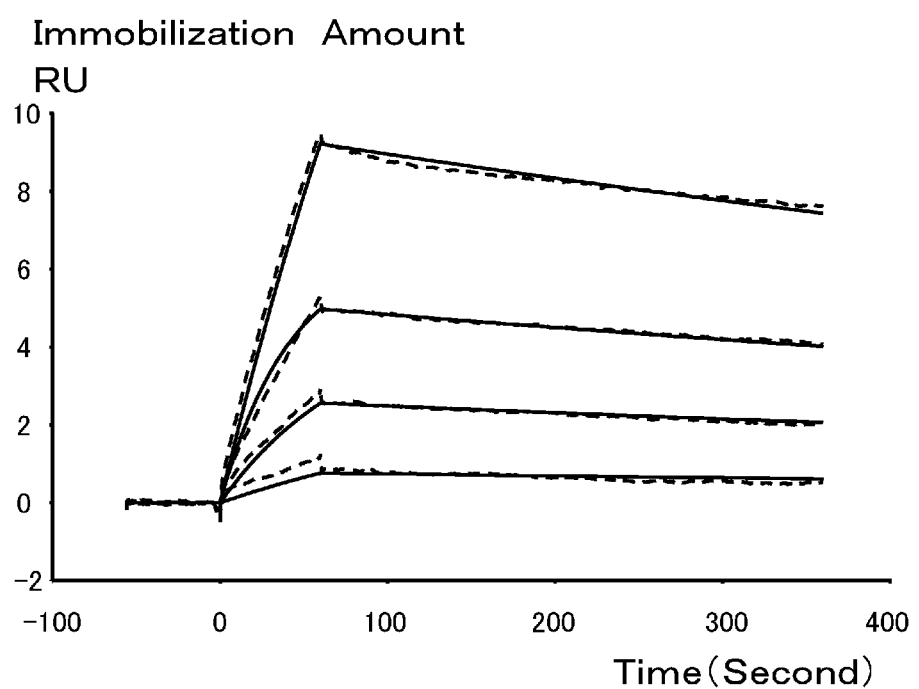
FIG. 4 is a graph showing a SPR evaluation result in a case of using the VHH antibody consisting of the amino acid sequence represented by SEQ ID NO: 16.

A similar experiment was conducted, except that the anti-H1N1 antibody consisting of the amino acid sequence represented by SEQ ID NO: 16 was used in place of the anti-H1N1 antibody consisting of the amino acid sequence represented by SEQ ID NO: 15. FIG. 4 is a graph showing the evaluation result obtained from the SPR evaluation device T200. The dissociation constant Kd was 1.53 nM.

(D-2) ELISA Evaluation of Anti-H1N1 Antibody

The binding ability of the VHH antibody consisting of the amino acid sequence represented by SEQ ID NO: 15 or SEQ ID NO: 16 to the HA protein was evaluated by an ELISA measurement method.

Prepared was a solution containing the VHH antibody consisting of the amino acid sequence represented by SEQ ID NO: 15 at a concentration of 5 micrograms/milliliter. Hereinafter, this solution is referred to as "Solution A". The solution A was diluted four-fold with PBS containing 3% skim milk. In this way, a diluted solution B was obtained. A part of the diluted solution B was diluted four-fold again with the PBS containing 3% skim milk. In this way, a diluted solution C was obtained. This was repeated to obtain diluted solutions D-G.

The influenza A virus subtype H1N1 (strain A/Narita/1/2009 (H1N1), available from Hokkaido University, Faculty of Veterinary Medicine) was mixed with 0.5% Triton-X. The final concentration of the virus was 20 micrograms/milliliter.

In this way, a solution containing the virus was obtained. In addition, this solution was diluted four-fold.

The solution containing the virus (at a concentration of 5 micrograms/milliliter) was injected into wells of a 96-well microplate (MaxiSorp, Nunc). Each well included 50 microliters of the solution. The 96-well plate was left at rest at room temperature for two hours to immobilize the virus in the wells.

PBS containing 0.05% Tween 20 was injected into each well to wash the wells. The PBS had a pH of 7.4. The volume of the PBS injected into each well was 200 microliters. This was repeated twice.

PBS containing 3% skim milk (available from Wako Pure Chemical Industries, Ltd.) was injected into each well to block the virus. The volume of the PBS injected into each well was 200 microliters. The 96-well plate was left at rest at room temperature for one hour.

PBS containing 0.05% Tween 20 was injected into each well to wash the wells. The PBS had a pH of 7.4. The volume of the PBS injected into each well was 200 microliters. This was repeated twice.

The diluted solutions B-G were injected into each well. The volume of the solution injected into each well was 50 microliters. The 96-well plate was left at rest at room temperature. Thus, the VHH antibodies contained in the diluted solutions B-G bound to the HA protein of the virus contained in the wells.

The 96-well plate was left at rest at room temperature for one hour.

PBS containing 0.05% Tween 20 was injected into each well to wash the wells. The PBS had a pH of 7.4. The volume of the PBS injected into each well was 200 microliters. This was repeated twice. The 96-well plate was left at rest at room temperature for one hour.

Labeled antibodies (available from Sigma-Aldrich, trade name: Monoclonal ANTI-FLAG M2 HRP antibody produced in mouse) were diluted 10,000-fold with PBS. The thus-diluted labelled antibodies were injected into each well (50 microliters/well). Then, the 96-well plate was left at rest for one hour in a dark place.

PBS containing 0.05% Tween 20 was injected into each well to wash the we lls. The PBS had a pH of 7.4. The volume of the PBS injected into each well was 200 microliters. This was repeated twice. The 96-well plate was left at rest at room temperature for one hour.

The color-producing agent (available from Thermo Fischer Scientific, Inc., trade name: 1-step ultra TMB-ELISA) was injected into each well (50 microliters/well). The 96-well plate was left at rest for thirty minutes to cause the color-producing agent to react with the antibody.

A sulfuric acid aqueous solution (normal, i.e., 1N) was injected into each well at a concentration of 50 microliters/well to cease the reaction.

Figure 5:
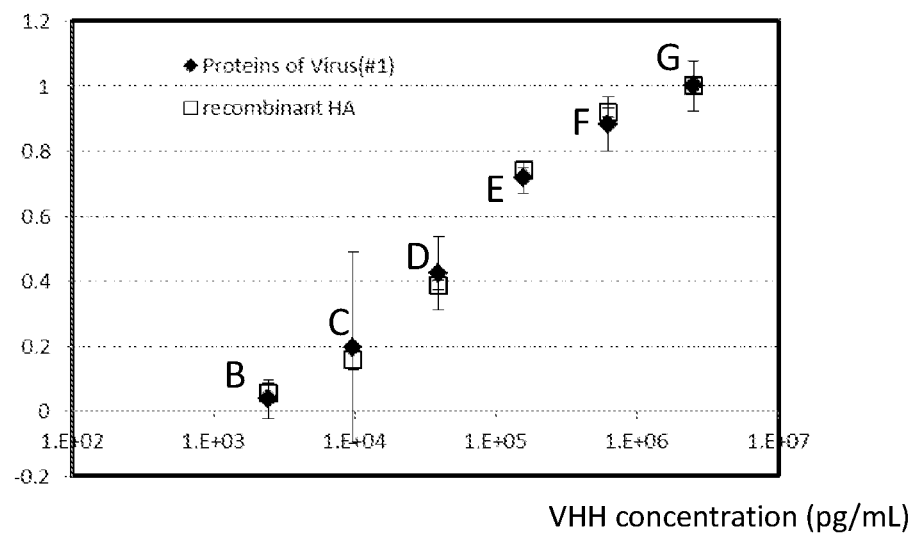
FIG. 5 is a graph showing an absorbance measurement result of a solution containing the VHH antibody consisting of the amino acid sequence represented by SEQ ID NO: 15 at a wavelength of 450 nanometers.
Figure 6:
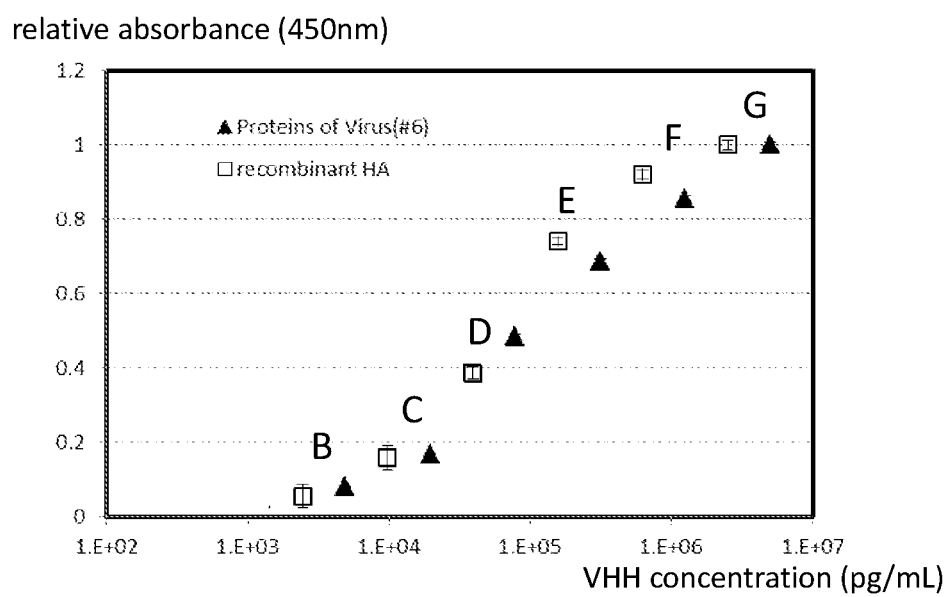
FIG. 6 is a graph showing an absorbance measurement result of a solution containing the VHH antibody consisting of the amino acid sequence represented by SEQ ID NO: 16 at a wavelength of 450 nanometers.

The absorbance of the solution at a wavelength of 450 nanometers was measured. FIG. 5 is a graph showing the measurement result of the VHH antibody consisting of the amino acid sequence represented by SEQ ID NO: 15. FIG. 6 is a graph showing the measurement result of the VHH antibody consisting of the amino acid sequence represented by SEQ ID NO: 16.

(D-3) Evaluation of Cross Reactivity to Other Influenza Virus Subtypes

The above-mentioned SPR evaluation device was used in order to evaluate the binding ability of the VHH antibody consisting of the amino acid sequence represented by SEQ ID NO: 15 or SEQ ID NO: 16 to the recombinant hemagglutinin (i.e., HA) proteins derived from the influenza A virus subtype H3N2, H5N1 and H7N9.

The recombinant hemagglutinin (i.e., HA) proteins derived from the influenza A virus subtype H3N2, H5N1 and H7N9 were available from Sino Biological Inc. as trade names: 40354-V08H1, 40160-V08H1, and 40104-V08H1, respectively. The immobilization amount of the hemagglutinin proteins was set to be approximately 200 RU.

Figure 7:
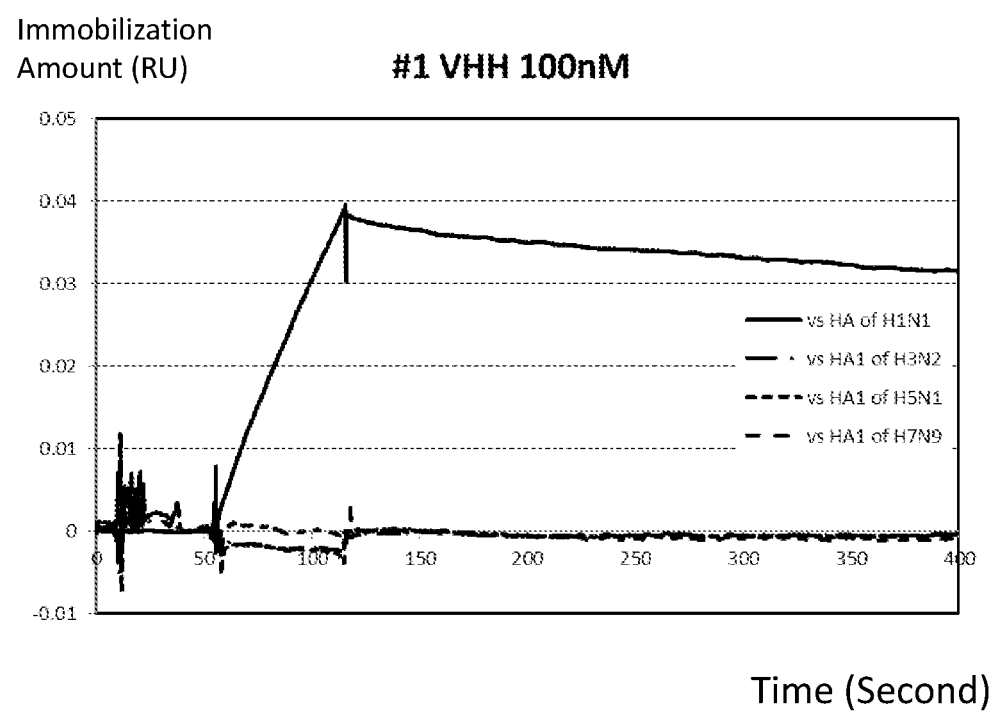
Figure 8:
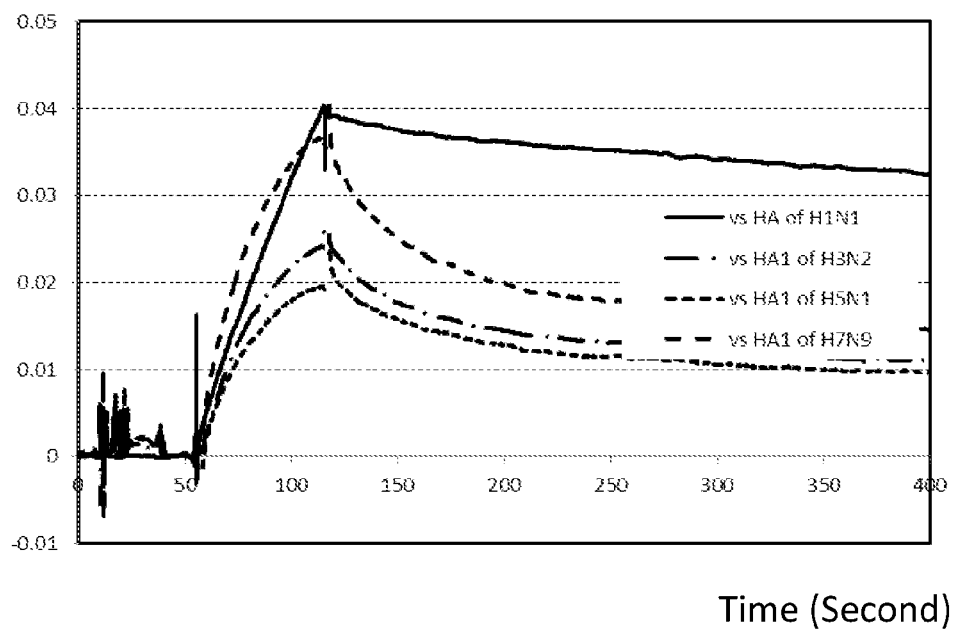
FIG. 8 is a graph showing a SPR measurement result of an interaction between the VHH antibody consisting of the amino acid sequence represented by SEQ ID NO: 16 and a recombinant hemagglutinin protein.

Using the SPR measurement device, the interaction between the VHH antibody (concentration: 100 nM) and the recombinant hemagglutinin protein was measured. FIG. 7 is a graph showing the measurement result of the VHH antibody consisting of the amino acid sequence represented by SEQ ID NO: 15. FIG. 8 is a graph showing the measurement result of the VHH antibody consisting of the amino acid sequence represented by SEQ ID NO: 16. In FIG. 7 and FIG. 8, the vertical axis indicates an amount of the VHH antibody bound to the immobilized antigen.

As understood from FIG. 7, the VHH antibody consisting of the amino acid sequence represented by SEQ ID NO: 15 has a low cross reactivity with regard to the recombinant hemagglutinin proteins derived from the influenza A virus subtype H3N2, H5N1 and H7N9. On the other hand, as understood from FIG. 8, the VHH antibody consisting of the amino acid sequence represented by SEQ ID NO: 16 has a relatively high cross reactivity with regard to the recombinant hemagglutinin proteins derived from the influenza A virus subtype H3N2, H5N1 and H7N9.

INDUSTRIAL APPLICABILITY

The present invention provides a novel antibody capable of binding to an influenza virus.

The invention claimed is:

1. An antibody that consists of an amino acid sequence, wherein said amino acid sequence consists of, in an N- to C-direction, the following structural domains:
N-FR1-CDR1-FR2-CDR2-FR3-CDR3-FR4-C wherein
FR denotes a framework region amino acid sequence and CDR denotes a complementary determining region amino acid sequence;
the CDR1 consists of an amino acid sequence represented by GFTFERFDMG (SEQ ID NO: 1);
the CDR2 consists of an amino acid sequence represented by RFNSDDGRKSYADAVKG (SEQ ID NO: 3);
the CDR3 consists of an amino acid sequence represented by SQAYTSSTDTSSTDAEDR (SEQ ID NO: 5);
the FR1 consists of an amino acid sequence represented by EVQLVESGGGFVQPGGSLRLSCVAS (SEQ ID NO: 7);
the FR2 consists of an amino acid sequence represented by WVRQAPGKSLEWVS (SEQ ID NO: 8);
the FR3 consists of an amino acid sequence represented by RFAISRDNAENTLYLQMNNLIPEDTATYYCVK (SEQ ID NO: 9);
the FR4 consists of an amino acid sequence represented by GQGTQVTVSSEPKTPKPQSA (SEQ ID NO: 10); and
the antibody is capable of binding to an H1N1 influenza virus.

2. An antibody that consists of an amino acid sequence, wherein said amino acid sequence consists of, in an N- to C-direction, the following structural domains:
N-FR1-CDR1-FR2-CDR2-FR3-CDR3-FR4-C wherein
FR denotes a framework region amino acid sequence and CDR denotes a complementary determining region amino acid sequence;
the CDR1 consists of an amino acid sequence represented by GRTFGAPYMA (SEQ ID NO: 2);
the CDR2 consists of an amino acid sequence represented by GDSTYYADSMKN (SEQ ID NO: 4);
the CDR3 consists of an amino acid sequence represented by DKWPFTGDVRSAGGYDY (SEQ ID NO: 6);
the FR1 consists of an amino acid sequence represented by QVQLVESGGGLVQAGDSLRLSCAAA (SEQ ID NO: 11);
the FR2 consists of an amino acid sequence represented by WFRQAPGKEREFVAGISWS (SEQ ID NO: 12);
the FR3 consists of an amino acid sequence represented by RFTISRDNAKNTVYLQMNSLNPEDTAVYYCAA (SEQ ID NO: 13);
the FR4 consists of an amino acid sequence represented by WGQGTQVTVSSEPKTPKPQSA (SEQ ID NO: 14); and
the antibody is capable of binding to an H1N1 influenza virus.

\* \* \* \* \*

SEQUENCE LISTING

```
<160> NUMBER OF SEQ ID NOS: 37

<210> SEQ ID NO 1
<211> LENGTH: 10
<212> TYPE: PRT
<213> ORGANISM: Lama pacos

<400> SEQUENCE: 1

Gly Phe Thr Phe Glu Arg Phe Asp Met Gly
1               5                   10

<210> SEQ ID NO 2
<211> LENGTH: 10
```

```
<212> TYPE: PRT
<213> ORGANISM: Lama pacos

<400> SEQUENCE: 2

Gly Arg Thr Phe Gly Ala Pro Tyr Met Ala
1               5                  10

<210> SEQ ID NO 3
<211> LENGTH: 17
<212> TYPE: PRT
<213> ORGANISM: Lama pacos

<400> SEQUENCE: 3

Arg Phe Asn Ser Asp Asp Gly Arg Lys Ser Tyr Ala Asp Ala Val Lys
1               5                  10                  15

Gly

<210> SEQ ID NO 4
<211> LENGTH: 12
<212> TYPE: PRT
<213> ORGANISM: Lama pacos

<400> SEQUENCE: 4

Gly Asp Ser Thr Tyr Tyr Ala Asp Ser Met Lys Asn
1               5                  10

<210> SEQ ID NO 5
<211> LENGTH: 18
<212> TYPE: PRT
<213> ORGANISM: Lama pacos

<400> SEQUENCE: 5

Ser Gln Ala Tyr Thr Ser Ser Thr Asp Thr Ser Thr Asp Ala Glu
1               5                  10                  15

Asp Arg

<210> SEQ ID NO 6
<211> LENGTH: 17
<212> TYPE: PRT
<213> ORGANISM: Lama pacos

<400> SEQUENCE: 6

Asp Lys Trp Pro Phe Thr Gly Asp Val Arg Ser Ala Gly Gly Tyr Asp
1               5                  10                  15

Tyr

<210> SEQ ID NO 7
<211> LENGTH: 25
<212> TYPE: PRT
<213> ORGANISM: Lama pacos

<400> SEQUENCE: 7

Glu Val Gln Leu Val Glu Ser Gly Gly Gly Phe Val Gln Pro Gly Gly
1               5                  10                  15

Ser Leu Arg Leu Ser Cys Val Ala Ser
            20                  25

<210> SEQ ID NO 8
<211> LENGTH: 14
<212> TYPE: PRT
<213> ORGANISM: Lama pacos

<400> SEQUENCE: 8
```

```
Trp Val Arg Gln Ala Pro Gly Lys Ser Leu Glu Trp Val Ser
1               5                   10
```

<210> SEQ ID NO 9
<211> LENGTH: 32
<212> TYPE: PRT
<213> ORGANISM: Lama pacos

<400> SEQUENCE: 9

```
Arg Phe Ala Ile Ser Arg Asp Asn Ala Glu Asn Thr Leu Tyr Leu Gln
1               5                   10                  15

Met Asn Asn Leu Ile Pro Glu Asp Thr Ala Thr Tyr Tyr Cys Val Lys
                20                  25                  30
```

<210> SEQ ID NO 10
<211> LENGTH: 20
<212> TYPE: PRT
<213> ORGANISM: Lama pacos

<400> SEQUENCE: 10

```
Gly Gln Gly Thr Gln Val Thr Val Ser Ser Glu Pro Lys Thr Pro Lys
1               5                   10                  15

Pro Gln Ser Ala
            20
```

<210> SEQ ID NO 11
<211> LENGTH: 25
<212> TYPE: PRT
<213> ORGANISM: Lama pacos

<400> SEQUENCE: 11

```
Gln Val Gln Leu Val Glu Ser Gly Gly Gly Leu Val Gln Ala Gly Asp
1               5                   10                  15

Ser Leu Arg Leu Ser Cys Ala Ala Ala
                20                  25
```

<210> SEQ ID NO 12
<211> LENGTH: 19
<212> TYPE: PRT
<213> ORGANISM: Lama pacos

<400> SEQUENCE: 12

```
Trp Phe Arg Gln Ala Pro Gly Lys Glu Arg Glu Phe Val Ala Gly Ile
1               5                   10                  15

Ser Trp Ser
```

<210> SEQ ID NO 13
<211> LENGTH: 32
<212> TYPE: PRT
<213> ORGANISM: Vicugna pacos

<400> SEQUENCE: 13

```
Arg Phe Thr Ile Ser Arg Asp Asn Ala Lys Asn Thr Val Tyr Leu Gln
1               5                   10                  15

Met Asn Ser Leu Asn Pro Glu Asp Thr Ala Val Tyr Tyr Cys Ala Ala
                20                  25                  30
```

<210> SEQ ID NO 14
<211> LENGTH: 21
<212> TYPE: PRT
<213> ORGANISM: Lama pacos

```
<400> SEQUENCE: 14

Trp Gly Gln Gly Thr Gln Val Thr Val Ser Ser Glu Pro Lys Thr Pro
1               5                   10                  15

Lys Pro Gln Ser Ala
            20

<210> SEQ ID NO 15
<211> LENGTH: 136
<212> TYPE: PRT
<213> ORGANISM: Lama pacos

<400> SEQUENCE: 15

Glu Val Gln Leu Val Glu Ser Gly Gly Gly Phe Val Gln Pro Gly Gly
1               5                   10                  15

Ser Leu Arg Leu Ser Cys Val Ala Ser Gly Phe Thr Phe Glu Arg Phe
            20                  25                  30

Asp Met Gly Trp Val Arg Gln Ala Pro Gly Lys Ser Leu Glu Trp Val
        35                  40                  45

Ser Arg Phe Asn Ser Asp Asp Gly Arg Lys Ser Tyr Ala Asp Ala Val
    50                  55                  60

Lys Gly Arg Phe Ala Ile Ser Arg Asp Asn Ala Glu Asn Thr Leu Tyr
65                  70                  75                  80

Leu Gln Met Asn Asn Leu Ile Pro Glu Asp Thr Ala Thr Tyr Tyr Cys
                85                  90                  95

Val Lys Ser Gln Ala Tyr Thr Ser Ser Thr Asp Thr Ser Ser Thr Asp
            100                 105                 110

Ala Glu Asp Arg Gly Gln Gly Thr Gln Val Thr Val Ser Ser Glu Pro
        115                 120                 125

Lys Thr Pro Lys Pro Gln Ser Ala
    130                 135

<210> SEQ ID NO 16
<211> LENGTH: 136
<212> TYPE: PRT
<213> ORGANISM: Lama pacos

<400> SEQUENCE: 16

Gln Val Gln Leu Val Glu Ser Gly Gly Gly Leu Val Gln Ala Gly Asp
1               5                   10                  15

Ser Leu Arg Leu Ser Cys Ala Ala Ala Gly Arg Thr Phe Gly Ala Pro
            20                  25                  30

Tyr Met Ala Trp Phe Arg Gln Ala Pro Gly Lys Glu Arg Glu Phe Val
        35                  40                  45

Ala Gly Ile Ser Trp Ser Gly Asp Ser Thr Tyr Tyr Ala Asp Ser Met
    50                  55                  60

Lys Asn Arg Phe Thr Ile Ser Arg Asp Asn Ala Lys Asn Thr Val Tyr
65                  70                  75                  80

Leu Gln Met Asn Ser Leu Asn Pro Glu Asp Thr Ala Val Tyr Tyr Cys
                85                  90                  95

Ala Ala Asp Lys Trp Pro Phe Thr Gly Asp Val Arg Ser Ala Gly Gly
            100                 105                 110

Tyr Asp Tyr Trp Gly Gln Gly Thr Gln Val Thr Val Ser Ser Glu Pro
        115                 120                 125

Lys Thr Pro Lys Pro Gln Ser Ala
    130                 135
```

```
<210> SEQ ID NO 17
<211> LENGTH: 15
<212> TYPE: DNA
<213> ORGANISM: Artificial Sequence
<220> FEATURE:
<223> OTHER INFORMATION: Synthesized Primer

<400> SEQUENCE: 17
ggtggtcctg gctgc                                                    15

<210> SEQ ID NO 18
<211> LENGTH: 50
<212> TYPE: DNA
<213> ORGANISM: Artificial Sequence
<220> FEATURE:
<223> OTHER INFORMATION: Synthesized Primer

<400> SEQUENCE: 18
ctgctcctcg cggcccagcc ggccatggct sagktgcagc tcgtggagtc              50

<210> SEQ ID NO 19
<211> LENGTH: 21
<212> TYPE: DNA
<213> ORGANISM: Artificial Sequence
<220> FEATURE:
<223> OTHER INFORMATION: Synthesized Primer

<400> SEQUENCE: 19
tggggtcttc gctgtggtgc g                                             21

<210> SEQ ID NO 20
<211> LENGTH: 21
<212> TYPE: DNA
<213> ORGANISM: Artificial Sequence
<220> FEATURE:
<223> OTHER INFORMATION: Synthesized Primer

<400> SEQUENCE: 20
ttgtggtttt ggtgtcttgg g                                             21

<210> SEQ ID NO 21
<211> LENGTH: 45
<212> TYPE: DNA
<213> ORGANISM: Artificial Sequence
<220> FEATURE:
<223> OTHER INFORMATION: Synthesized Primer

<400> SEQUENCE: 21
tttgctctgc ggccgcagag gccgtggggt cttcgctgtg gtgcg                   45

<210> SEQ ID NO 22
<211> LENGTH: 46
<212> TYPE: DNA
<213> ORGANISM: Artificial Sequence
<220> FEATURE:
<223> OTHER INFORMATION: Synthesized Primer

<400> SEQUENCE: 22
tttgctctgc ggccgcagag gccgattgtg gttttggtgt cttggg                  46

<210> SEQ ID NO 23
<211> LENGTH: 13
<212> TYPE: DNA
<213> ORGANISM: Artificial Sequence
<220> FEATURE:
<223> OTHER INFORMATION: Synthesized DNA which represents SfiI(a) site
```

```
<400> SEQUENCE: 23
ggcccagccg gcc                                                            13

<210> SEQ ID NO 24
<211> LENGTH: 13
<212> TYPE: DNA
<213> ORGANISM: Artificial Sequence
<220> FEATURE:
<223> OTHER INFORMATION: Synthesized DNA which represents SfiI(b) site

<400> SEQUENCE: 24
ggcctctgcg gcc                                                            13

<210> SEQ ID NO 25
<211> LENGTH: 4057
<212> TYPE: DNA
<213> ORGANISM: Artificial Sequence
<220> FEATURE:
<223> OTHER INFORMATION: Synthesized plamid Vector 1

<400> SEQUENCE: 25
gacgaaaggg cctcgtgata cgcctatttt tataggttaa tgtcatgata ataatggttt         60
cttagacgtc aggtggcact tttcggggaa atgtgcgcgg aacccctatt tgtttatttt        120
tctaaataca ttcaaatatg tatccgctca tgagacaata accctgataa atgcttcaat        180
aatattgaaa aaggaagagt atgagtattc aacatttccg tgtcgccctt attccctttt        240
ttgcggcatt ttgccttcct gttttgctc acccagaaac gctggtgaaa gtaaaagatg         300
ctgaagatca gttgggtgca cgagtgggtt acatcgaact ggatctcaac agcggtaaga        360
tccttgagag ttttcgcccc gaagaacgtt ttccaatgat gagcactttt aaagttctgc        420
tatgtggcgc ggtattatcc cgtattgacg ccgggcaaga gcaactcggt cgccgcatac        480
actattctca gaatgacttg gttgagtact caccagtcac agaaaagcat cttacggatg        540
gcatgacagt aagagaatta tgcagtgctg ccataaccat gagtgataac actgcggcca        600
acttacttct gacaacgatc ggaggaccga aggagctaac cgcttttttg cacaacatgg        660
gggatcatgt aactcgcctt gatcgttggg aaccggagct gaatgaagcc ataccaaacg        720
acgagcgtga caccacgatg cctgtagcaa tggcaacaac gttgcgcaaa ctattaactg        780
gcgaactact tactctagct tcccggcaac aattaataga ctggatggag gcggataaag        840
ttgcaggacc acttctgcgc tcggcccttc cggctggctg gtttattgct gataaatctg        900
gagccggtga gcgtgggtct cgcggtatca ttgcagcact ggggccagat ggtaagccct        960
cccgtatcgt agttatctac acgacgggga gtcaggcaac tatggatgaa cgaaatagac       1020
agatcgctga gataggtgcc tcactgatta agcattggta actgtcagac caagtttact       1080
catatatact ttagattgat ttaaaacttc atttttaatt taaaaggatc taggtgaaga       1140
tcctttttga atctcatg accaaaatcc cttaacgtga gttttcgttc cactgagcgt        1200
cagaccccgt agaaaagatc aaaggatctt cttgagatcc tttttttctg cgcgtaatct       1260
gctgcttgca acaaaaaaa ccaccgctac cagcggtggt ttgtttgccg gatcaagagc       1320
taccaactct ttttccgaag gtaactggct tcagcagagc gcagatacca atactgtcc        1380 ttctagtgta gccgtagtta ggccaccact tcaagaactc tgtagcaccg cctacatacc       1440
tcgctctgct aatcctgtta ccagtggctg ctgccagtgg cgataagtcg tgtcttaccg       1500
ggttggactc aagacgatag ttaccggata aggcgcagcg gtcgggctga acggggggt        1560 cgtgcacaca gcccagcttg gagcgaacga cctacaccga actgagatac ctacagcgtg       1620
```

```
agctatgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag     1800 gggggcggag cctatggaaa aacgccagca acgcggcctt tttacggttc ctggcctttt    1860
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgccaagctt cgaaggagac agtcataatg aaatacctgc tgccgaccgc    2280
tgctgctggt ctgctgctcc tcgcggccca gccggccatg gagctcaaga tgacacagac    2340
tacatcctcc ctgtcagcct ctctgggaga cagagtcacc atcagttgca gggcaagtca    2400
ggacattagc gattatttaa actggtatca gcagaaacca gatggaactg ttaaactcct    2460
gatctattac acatcaagtt tacactcagg agtcccatca aggttcagtg gcggtgggtc    2520
tggaacagat tattctctca ccattagcaa cctggagcaa gaagatattg ccacttactt    2580
ttgccaacag ggtaatacgc ttccgtggac gtttggtgga ggcaccaagc tggaaatcaa    2640
acgggctgat gctgcaccaa ctgtaggcct ctgcggccgc agagcaaaaa ctcatctcag    2700
aagaggatct gaatggggcc gcatagggtt ccggtgattt tgattatgaa aagatggcaa    2760
acgctaataa gggggctatg accgaaaatg ccgatgaaaa cgcgctacag tctgacgcta    2820
aaggcaaact tgattctgtc gctactgatt acggtgctgc tatcgatggt ttcattggtg    2880
acgtttccgg ccttgctaat ggtaatggtg ctactggtga ttttgctggc tctaattccc    2940
aaatggctca agtcggtgac ggtgataatt cacctttaat gaataatttc cgtcaatatt    3000
taccttccct ccctcaatcg gttgaatgtc gcccttttgt ctttagcgct ggtaaaccat    3060
atgaattttc tattgattgt gacaaaataa acttattccg tggtgtcttt gcgtttcttt    3120
tatatgttgc cacctttatg tatgtatttt ctacgtttgc taacatactg cgtaataagg    3180
agtcttaata agaattcact ggccgtcgtt ttacaacgtc gtgactggga aaaccctggc    3240
gttacccaac ttaatcgcct tgcagcacat ccccctttcg ccagctggcg taatagcgaa    3300
gaggcccgca ccgatcgccc ttcccaacag ttgcgcagcc tgaatggcga atggcgcctg    3360
atgcggtatt ttctccttac gcatctgtgc ggtatttcac accgcatatg aaaattgtaa    3420
gcgttaatat tttgttaaaa ttcgcgttaa attttgttta atcagctca ttttttaacc     3480 aataggccga atcggcaaa atcccttata atcaaaaga atagaccgag atagggttga     3540
gtgttgttcc agtttggaac aagagtccac tattaaagaa cgtggactcc aacgtcaaag    3600
ggcgaaaaac cgtctatcag ggcgatggcc cactacgtga accatcaccc taatcaagtt    3660
ttttggggtc gaggtgccgt aaagcactaa atcggaaccc taaagggagc ccccgattta    3720
gagcttgacg gggaaagccg gcgaacgtgg cgagaaagga agggaagaaa gcgaaaggag    3780
cgggcgctag ggcgctggca agtgtagcgg tcacgctgcg cgtaaccacc acacccgccg    3840
cgcttaatgc gccgctacag ggcgcgtccc atatggcga ctctcagtac aatctgctct     3900
gatgccgcat agttaagcca gccccgacac ccgccaacac ccgctgacgc gccctgacgg    3960
```

```
gcttgtctgc tcccggcatc cgcttacaga caagctgtga ccgtctccgg gagctgcatg   4020
tgtcagaggt tttcaccgtc atcaccgaaa cgcgcga                            4057
```

<210> SEQ ID NO 26
<211> LENGTH: 408
<212> TYPE: DNA
<213> ORGANISM: Artificial Sequence
<220> FEATURE:
<223> OTHER INFORMATION: Synthesized DNA coding for anti-H1N1 VHH
      antibody

<400> SEQUENCE: 26

```
gaggtgcagc tcgtggagtc tgggggaggc tttgtgcagc cggggggggtc cctgagactc    60 tcctgtgtag cctctggatt cacgttcgag cgttttgaca tgggttgggt ccgccaggct   120
ccgggaaaaa gcctcgagtg gtctcgcgt tttaatagtg atgatggtcg aaaaagttat    180
gcggacgccg tgaagggccg attcgccatt tccagagaca cgccgaaaaa cacgctatat   240
ctacaaatga caatctgat acctgaagac acggccactt attattgtgt gaagtctcaa    300
gcttacacat cttctactga tacatcttct actgatgccg aagacagggg ccaggggacc   360
caggtcaccg tctcctcgga acccaagaca ccaaaaccac aatcggcc                408
```

<210> SEQ ID NO 27
<211> LENGTH: 408
<212> TYPE: DNA
<213> ORGANISM: Artificial Sequence
<220> FEATURE:
<223> OTHER INFORMATION: Synthesized DNA coding for anti-N1H1 VHH
      antibody

<400> SEQUENCE: 27

```
caggtgcagc tcgtggagtc tgggggagga ttggtgcagg ctggggactc tctgagactc    60
tcctgtgcgg ccgctggacg caccttcggt gcaccttaca tggcctggtt ccgccaggct   120
ccagggaagg agcgtgaatt tgtagcaggt atatcttgga gtggtgatag cacatactat   180
gcagactcca tgaagaaccg gttcaccatc tccagagaca cgccaagaa cacggtgtat    240 ctgcaaatga cagcctaaa ccctgaggac acggccgttt attactgtgc agcggataag    300 tggccctta ccggtgatgt gcggtccgcg gggggggtatg actactgggg ccaggggacc   360
caggtcaccg tctcctcaga acccaagaca ccaaaaccac aatcggcc                408
```

<210> SEQ ID NO 28
<211> LENGTH: 30
<212> TYPE: DNA
<213> ORGANISM: Artificial Sequence
<220> FEATURE:
<223> OTHER INFORMATION: Synthesized Primer

<400> SEQUENCE: 28

```
gccggctggg ccgcgaggag cagcagacca                                     30
```

<210> SEQ ID NO 29
<211> LENGTH: 30
<212> TYPE: DNA
<213> ORGANISM: Artificial Sequence
<220> FEATURE:
<223> OTHER INFORMATION: Synthesized Primer

<400> SEQUENCE: 29

```
gcccagccgg ccatggccat ggatatcgga                                     30
```

```
<210> SEQ ID NO 30
<211> LENGTH: 96
<212> TYPE: DNA
<213> ORGANISM: Artificial Sequence
<220> FEATURE:
<223> OTHER INFORMATION: Synthesized Primer

<400> SEQUENCE: 30
catggatatc ggaattaatt cggatccgac tacaaagacc atgacggtga ttataaagat    60
catgacatcc tcgagcacca ccaccaccac cactga                              96

<210> SEQ ID NO 31
<211> LENGTH: 96
<212> TYPE: DNA
<213> ORGANISM: Artificial Sequence
<220> FEATURE:
<223> OTHER INFORMATION: Synthesized Primer

<400> SEQUENCE: 31
tcagtggtgg tggtggtggt gctcgaggat gtcatgatct ttataatcac cgtcatggtc    60
tttgtagtcg gatccgaatt aattccgata tccatg                              96

<210> SEQ ID NO 32
<211> LENGTH: 74
<212> TYPE: DNA
<213> ORGANISM: Artificial Sequence
<220> FEATURE:
<223> OTHER INFORMATION: Synthesized Primer

<400> SEQUENCE: 32
aaatacctgc tgccgccatg gatatcggaa ttaattcggc ctctgcggcc gcaggatccg    60
actacaaaga ccat                                                      74

<210> SEQ ID NO 33
<211> LENGTH: 74
<212> TYPE: DNA
<213> ORGANISM: Artificial Sequence
<220> FEATURE:
<223> OTHER INFORMATION: Synthesized Primer

<400> SEQUENCE: 33
atggtctttg tagtcggatc ctgcggccgc agaggccgaa ttaattccga tatccatggc    60
ggcagcaggt attt                                                      74

<210> SEQ ID NO 34
<211> LENGTH: 436
<212> TYPE: DNA
<213> ORGANISM: Artificial Sequence
<220> FEATURE:
<223> OTHER INFORMATION: Synthesized DNA including the gene sequence
      coding for the amino acid sequence represented by SEQ ID NO: 15

<400> SEQUENCE: 34
ggcccagccg gccatggctg aggtgcagct cgtggagtct gggggaggct tgtgcagcc     60 ggggggggtcc ctgagactct cctgtgtagc ctctggattc acgttcgagc gttttgacat   120
gggttgggtc cgccaggctc cgggaaaaag cctcgagtgg gtctcgcgtt ttaatagtga   180
tgatggtcga aaaagttatg cggacgccgt gaagggccga ttcgccattt ccagagacaa   240
cgccgaaaac acgctatatc tacaaatgaa caatctgata cctgaagaca cggccactta   300
```

```
ttattgtgtg aagtctcaag cttacacatc ttctactgat acatcttcta ctgatgccga    360 agacagggc caggggaccc aggtcaccgt ctcctcggaa cccaagacac caaaaccaca    420
atcggcctct gcggcc                                                    436
```

<210> SEQ ID NO 35
<211> LENGTH: 436
<212> TYPE: DNA
<213> ORGANISM: Artificial Sequence
<220> FEATURE:
<223> OTHER INFORMATION: Synthesized DNA including the gene sequence
      coding for the amino acid sequence represented by SEQ ID NO: 16

<400> SEQUENCE: 35

```
ggcccagccg gccatggctc aggtgcagct cgtggagtct gggggaggat tggtgcaggc    60
tggggactct ctgagactct cctgtgcggc cgctggacgc accttcggtg caccttacat    120
ggcctggttc cgccaggctc cagggaagga gcgtgaattt gtagcaggta tatcttggag    180
tggtgatagc acatactatg cagactccat gaagaaccgg ttcaccatct ccagagacaa    240
cgccaagaac acggtgtatc tgcaaatgaa cagcctaaac cctgaggaca cggccgttta    300
ttactgtgca gcggataagt ggccctttac cggtgatgtg cggtccgcgg ggggtatga    360 ctactggggc caggggaccc aggtcaccgt ctcctcagaa cccaagacac caaaaccaca    420
atcggcctct gcggcc                                                    436
```

<210> SEQ ID NO 36
<211> LENGTH: 423
<212> TYPE: DNA
<213> ORGANISM: Artificial Sequence
<220> FEATURE:
<223> OTHER INFORMATION: Synthesized DNA obtained by SfiI-treating the
      DNA represented by SEQ ID NO: 34

<400> SEQUENCE: 36

```
cggccatggc tgaggtgcag ctcgtggagt ctgggggagg ctttgtgcag ccggggggt    60 ccctgagact ctcctgtgta gcctctggat tcacgttcga gcgttttgac atgggttggg    120
tccgccaggc tccgggaaaa agcctcgagt gggtctcgcg tttttaatagt gatgatggtc    180 gaaaaagtta tgcggacgcc gtgaagggcc gattcgccat ttccagagac aacgccgaaa    240
acacgctata tctacaaatg aacaatctga tacctgaaga cacggccact tattattgtg    300
tgaagtctca agcttacaca tcttctactg atacatcttc tactgatgcc gaagacaggg    360
gccaggggac ccaggtcacc gtctcctcgg aacccaagac accaaaacca caatcggcct    420
ctg                                                                  423
```

<210> SEQ ID NO 37
<211> LENGTH: 423
<212> TYPE: DNA
<213> ORGANISM: Artificial Sequence
<220> FEATURE:
<223> OTHER INFORMATION: Synthesized DNA obtained by SfiI-treating the
      DNA represented by SEQ ID NO: 35

<400> SEQUENCE: 37

```
cggccatggc tcaggtgcag ctcgtggagt ctgggggagg attggtgcag gctggggact    60
ctctgagact ctcctgtgcg gccgctggac gcaccttcgg tgcaccttac atggcctggt    120
tccgccaggc tccagggaag gagcgtgaat ttgtagcagg tatatcttgg agtggtgata    180
gcacatacta tgcagactcc atgaagaacc ggttcaccat ctccagagac aacgccaaga    240
```

```
acacggtgta tctgcaaatg aacagcctaa accctgagga cacggccgtt tattactgtg    300
cagcggataa gtggcccttt accggtgatg tgcggtccgc ggggggtat gactactggg     360 gccaggggac ccaggtcacc gtctcctcag aacccaagac accaaaacca caatcggcct    420
ctg                                                                  423
```